United States Patent [19]

Baggaley

[11] 4,350,702

[45] Sep. 21, 1982

[54] METHOD OF INHIBITING PLATELET AGGREGATION

[75] Inventor: Keith H. Baggaley, Redhill, England

[73] Assignee: Beecham Group Limited, England

[21] Appl. No.: 202,711

[22] Filed: Oct. 31, 1980

Related U.S. Application Data

[60] Continuation of Ser. No. 850,788, Nov. 11, 1977, abandoned, which is a division of Ser. No. 738,000, Nov. 2, 1976, Pat. No. 4,113,728.

[30] Foreign Application Priority Data

Nov. 18, 1975 [GB] United Kingdom ............... 47373/75

[51] Int. Cl.$^3$ ............................................ A61K 31/425
[52] U.S. Cl. ..................................... 424/270; 548/209

[58] Field of Search ......................... 548/209; 424/270

[56] References Cited

U.S. PATENT DOCUMENTS

| | | | |
|---|---|---|---|
| 4,182,768 | 1/1980 | Nunn et al. | 424/270 |
| 4,206,217 | 1/1980 | Aagen et al. | 544/333 |
| 4,243,669 | 1/1981 | Baggaley | 548/209 |

*Primary Examiner*—Nicholas S. Rizzo
*Attorney, Agent, or Firm*—Jacobs & Jacobs

[57] ABSTRACT

A class of 2-substituted benzisothiazolones carrying a nitrogen-containing heterocyclic ring are effective in inhibiting platelet aggregation and are therefore of value in the prophylactic and therapeutic treatment of thrombotic diseases.

19 Claims, No Drawings

METHOD OF INHIBITING PLATELET AGGREGATION

This is a continuation of Ser. No. 850,788 filed Nov. 11, 1977 and now abandoned, which was a divisional of Ser. No. 738,000, filed Nov. 2, 1976, now U.S. Pat. No. 4,113,728, issued Sept. 12, 1978.

This invention relates to a class of benzisothiazolones which are of value in the prophylactic and therapeutic treatment of thrombotic diseases. The invention also relates to a method for the preparation of such compounds and to pharmaceutical compositions comprising them.

Arterial thrombosis develops initially from the aggregation of blood platelets within the artery. This aggregate may eventually lead to the formation of fibrin and the formation of a consolidated occlusive thrombus. The most widely used therapy for thrombosis is the use of anti-coagulant agents, which influence blood clotting. However, although effective in venous thrombosis, where the thrombus is formed mainly of fibrin, anti-coagulant therapy has no effect on platelet aggregation and has therefore limited effectiveness in arterial thrombosis. It is now accepted that anti-coagulant drugs have little to offer in the treatment of arterial thrombosis.

With the increasing recognition of the primary role of platelets in thrombosis, attention had turned to drugs which are capable of inhibiting the aggregation of platelets.

It has now been found that a class of benzisothiazolones are effective in inhibiting platelet aggregation.

Accordingly the present invention provides a compound of formula (I) or a pharmaceutically acceptable non-toxic acid addition salt thereof when there is a basic nitrogen atom in the molecule:

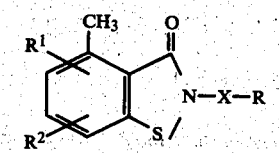

wherein $R^1$ and $R^2$ are the same or different and each is hydrogen, lower alkyl, lower alkoxy, halo-lower alkyl, nitro, amino, acylamino, or halogen, or $R^1$ together with $R^2$ when attached to adjacent carbon atoms represent a $C_3$–$C_6$ alkylene or oxy($C_1$–$C_3$)alkyleneoxy moiety; X represents a bond or a straight or branched chain alkylene group having from one to twelve carbon atoms; and R represents a nitrogen-containing heterocyclic ring, or a group of formula —NH.$R^3$ wherein $R^3$ is a nitrogen-containing heterocyclic ring, the groups R and $R^3$ being optionally substituted with a lower alkyl, carboxy or alkoxycarbonyl group; provided that,
(a) when X represents a bond, R is not a pyridmidyl, pyridyl or thiazolinyl or benzthiazolyl group; and
(b) when $R^1$ and $R^2$ are at positions 5 and 7 and are hydrogen or halogen and X is a lower alkylene group, then R is not a piperidinyl, pyrrolidinyl, morpholinyl or piperazinyl group which is attached via a nitrogen atom thereof to the group X.

Suitable acid addition salts include inorganic salts such as the sulphate, nitrate, phosphate, and borate, hydrohalides e.g. hydrochloride, hydrobromide, and hydroiodide, and organic acid addition salts such as acetate, oxalate, tartrate, maleate, citrate, succinate, benzoate, ascorbate, methanesulphonate and p-toluenesulphonate.

Suitable groups for the substituents $R^1$ and $R^2$ include methyl, ethyl, n- and iso-propyl, n-, sec-, iso, and tert-butyl, methoxy, ethoxy, n- and iso-propoxy, n-, sec-, iso- and tert-butoxy, chloro, bromo fluoro, t fluoromethyl. Preferably $R^1$ is hydrogen or a methyl group or chlorine atom. When neither $R^1$ nor $R^2$ are hydrogen, they are preferably lower alkyl or lower alkoxy, especially methyl or methoxy.

Preferably, $R^1$ and $R^2$ are at positions 5 and 6 respectively. In one suitable class of compounds, the substituent at position 5 is a lower alkyl.

Suitable alkylene groups for the group X include, for example, methylene, ethylene, propylene, n-butylene, n-pentylene, n-hexylene, n-dodecylene, 1-methylethylene, 1- or 2-methylpropylene, isopropylene, isobutylene. Preferably, the group X has from 1 to 6 carbon atoms, especially two carbon atoms.

When either group R or $R^3$ is a nitrogen-containing heterocyclic ring, such a ring may be aromatic or non-aromatic, and the attachment to the group X (in the case of group R) or the group NH (in the case of group $R^3$) may be via, for example, the nitrogen atom or a carbon atom. The ring may also contain other hetero atoms, for example oxygen or sulphur. The group R or $R^3$ may represent single or polycyclic rings and may comprise a total of from 5 to 12 atoms. Examples of such rings include pyrimidyl, 2-, 3- or 4-pyridyl, pyrrolyl, thiazolyl, thiazolinyl, diazolyl, triazolyl, tetrazolyl, thiatriazolyl, oxazolyl, oxadiazolyl, purinyl, tetrahydroquinolyl, tetrahydroisoquinolyl, benzimidazolyl, benzoxazolyl, benzthiazolyl, benzisothiazolonyl, piperidinyl, pyrrolidinyl, morpholinyl, piperazinyl, 3-azabicyclo [3.2.2] non-3-yl, 9-azabicyclo [3.3.1] non-9-yl, homopiperidinyl, 2-azabicyclo [2.2.2] non-2-yl. Suitably R or $R^3$ represents 2-pyridyl, 1-pyrrolidinyl, 1-piperidinyl, 1-homopiperidinyl 2-methylpiperidin-1-yl, 3-azabicyclo [3.2.2] non-3-yl, tetrahydroisoquinolyl.

The group R or $R^3$ may be optionally substituted with a lower alkyl, carboxy or alkoxycarbonyl group. Preferred alkoxycarbonyl groups are $C_{1-6}$ alkoxycarbonyl groups for example methoxycarbonyl, ethoxycarbonyl, n- and iso-propoxycarbonyl, n-, iso-, sec- and tert-butoxycarbonyl. Preferred lower alkyl groups include methyl and ethyl, especially methyl.

From the foregoing it may be seen that one suitable class of compounds according to this invention are compounds of formula (II) and pharmaceutically acceptable non-toxic acid addition salts thereof:

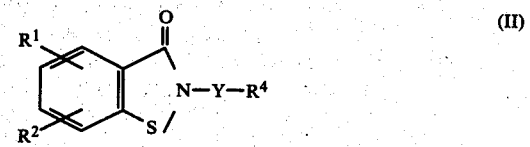

wherein $R^1$ and $R^2$ are as defined with respect to formula (I) above. Y is a straight-or branched-alkylene chain having from one to twelve carbon atoms and $R^4$ is a nitrogen-containing aromatic ring. Suitable groups $R^4$ include pyrimidyl, pyridyl, thiazolyl. Specific compounds of formula (II) include the following:
2-(β-2′-pyridylethyl)-1,2-benzisothiazol-3-one;
2-(β-2′-pyridylethyl)-1,2-benzisothiazol-3-one hydrochloride;

6-chloro-2-(β-2′-pyridylethyl)-1,2-benzisothiazol-3-one hydrochloride;
5-chloro-2-(β-2′-pyridylethyl)-1,2-benzisothiazol-3-one hydrochloride;
5-methyl-2-(β-2′-pyridylethyl)-1,2-benzisothiazol-3-one hydrochloride;
5,6-dimethyl-2-(β-2′-pyridylethyl)-1,2-benzisothiazol-3-one;
6-nitro-2-(β-2′-pyridylethyl)-1,2-benzisothiazol-3-one;
6-amino-2-(β-2′-pyridylethyl)-1,2-benzisothiazol-3-one;
6-acetylamino-2-(β-2′-pyridylethyl)-1,2-benzisothiazol-3-one;
5,6-dichloro-2-(3′-pyridylmethyl)-1,2-benzisothiazol-3-one;
2-b-(4-methyl-2-thiazolyl)ethyl-1,2-benzisothiazol-3-one;
5-methyl-2-β-(4-methyl-2-thiazolyl)ethyl-1,2-benzisothiazol-3-one.

Another sub-class of compounds within the present invention comprises compounds of formula (III) and pharmaceutically acceptable non-toxic acid addition salts of such compounds having a basic nitrogen atom:

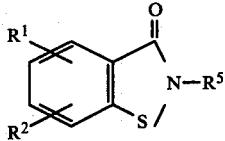

(III)

wherein $R^1$ and $R^2$ are as defined with respect to formula (I) above, and $R^5$ is thiazolyl, piperidinyl, pyrrolidinyl, morpholinyl, piperazinyl, 3-azabicyclo[3.2.2]-non-3-yl, 9-azabicyclo[3.3.1]non-9-yl, homopiperidinyl and 2-azabicyclo[2.2.2]non-2-yl.

Specific compounds of formula (III) include the following:
2-(morpholino)-1,2-benzisothiazol-3-one;
2-(thiazol-2-yl)-1,2-benzisothiazol-3-one;

A further class within this invention comprises compounds of formula (IV) and pharmaceutically acceptable non-toxic acid addition salts of such compounds having a basic nitrogen:

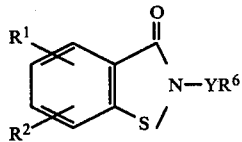

(IV)

wherein $R^1$ and $R^2$ are as defined with respect to formula (I) above, Y is a straight-or branched-alkylene chain having from one to twelve carbon atoms, and $R^6$ is 3-azabicyclo[3.2.2]non-3-yl, 9-azabicyclo[3.3.1]non-9-yl, homopiperidinyl and 2-azabicylo[2.2.2]non-2-yl, or 1,2-benzisothiazol-3-on-2-yl, tetrahydroisoquinolyl. Specific compounds of formula (IV) include the following:
2-β-(3-azabicyclo[3.2.2]non-3-yl)ethyl-1,2-benzisothiazol-3-one hydrochloride;
5,6-dichloro-2-β-(1-pyrrolidinyl)ethyl-1,2-benzisothiazol-3-one;
5,6-dichloro-2-β-(1-pyrrolidinyl)ethyl-1,2-benzisothiazol-3-one hydrochloride;
5,6-dichloro-2-β-(3-azabicyclo[3.2.2]non-3-yl)ethyl-1,2-benzisothiazol-3-one;

2-β-(homopiperidin-1-yl)ethyl-1,2-benzisothiazol-3-one hydrochloride;
1,2-bis(1,2-benzisothiazol-3-on-2-yl)ethane;
5,6-dimethoxy-2-β-(3-azabicyclo[3.2.2]non-3-yl)ethyl 1,2-benzisothiazol-3-one;
5,6-dimethyl-2-β-(3-azabicyclo[3.2.2]non-3-yl)ethyl 1,2-benzisothiazol-3-one;
2-β-(9-azabicyclo[3.3.1]non-9-yl)ethyl-1,2-benzisothiazol-3-one;
2-β-(N-tetrahydroisoquinolylethyl)-1,2-benzisothiazol-3-one hydrochloride.

Another group of compounds within the present invention have formula (V), and pharmaceutically acceptable acid addition salts of such compounds having a basic nitrogen atom:

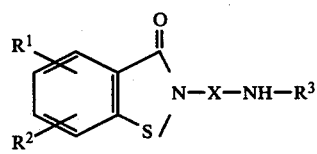

(V)

wherein $R^1$, $R^2$, $R^3$ and X are as defined with respect to formula (I) above. Specific compounds of formula (V) include the following:
2-[2′-pyridylaminomethyl]-1,2-benzisothiazol-3-one;
2-[4′-pyridylaminomethyl]-1,2-benzisothiazol-3-one;
2-[5′-ethoxycarbonylthiazol-2′-yl)aminomethyl]-1,2-benzisothiazol-3-one;

Other specific compounds falling within this invention include the following:
5-methyl-2-(β-1-pyrrolidinylethyl)-1,2-benzisothiazol-3-one oxalate;
5,6-dimethyl-2-(β-1-pyrrolidinylethyl)-1,2-benzisothiazol-3-one;
2-[β-(2-methyl-1-pyrrolidinyl)ethyl]-1,2-benzisothiazol-3-one.

The compounds of this invention may be prepared by reacting a compound of formula (VI):

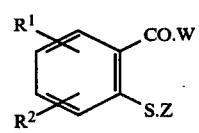

(VI)

wherein $R^1$ and $R^2$ are as defined with respect to formula (I) above, and W and Z are the same or different and each is a halogen atom; with a compound of formula (VII):

NH$_2$.X.R  (VII)

wherein X and R are as defined with respect to formula (I) above.

Preferably W is chlorine and Z is chlorine or bromine. Suitable solvents for the reaction include carbon tetrachloride or other halogenated hydrocarbon solvents.

A second method for the preparation of the compounds of formula (I) comprises reaction of a compound of formula (VIII) or a salt thereof:

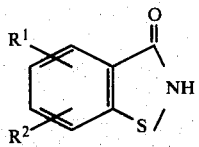
(VIII)

wherein $R^1$ and $R^2$ are as defined with respect to formula (I) above; and with a compound of formula (IX):

$$Q-X-R \qquad (IX)$$

wherein X and R are as defined with respect to formula (I) above and Q is a readily displaceable group. Suitably, Q is a halogen atom. Preferably the compound (VIII) is used as its alkali metal salt, for example the sodium salt.

In this reaction a solvent such as dimethyl formamide or dimethylsulphoxide may be used, preferably at elevated temperatures. In general the corresponding 3-ether is also formed and the desired product may be separated by crystallisation, distillation and chromatographic techniques.

The intermediate (IX) may if desired be formed in situ in the reaction. For example, for compounds of formula (I) wherein X represents a $CH_2$ group, this process may be operated by reacting compound (VIII) with an amine $R.NH_2$ in the presence of formaldehyde.

Compounds of formula (I) may also be prepared by treating a compound of formula (X):

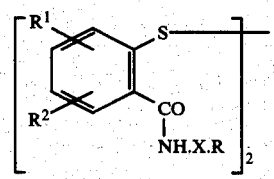
(X)

wherein $R^1$, $R^2$, X and R are as defined with respect to formula (I) above; with either a base or with chlorine or bromine.

Suitable bases include 10% sodium hydroxide or other aqueous alkali and the reaction may be carried out at room temperature or elevated temperatures. If chlorine is employed in this reaction it may be bubbled into a solution of compound (X) in an inert solvent such as carbon tetrachloride.

Compounds of formula (I) may also be prepared by treating a compound of formul (XI):

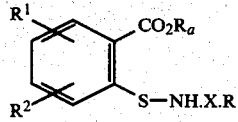
(XI)

wherein X, R, $R^1$ and $R^2$ are as defined with respect to formula (I) above and $CO_2R_a$ is a carboxylic ester group; with a base.

Suitably the group $R_a$ is an alkyl or aryl group. Suitable bases for the reaction include alkali metal alkoxides, alkali metal hydroxides and tetramethylammonium hydroxide in lower alcohols.

The compounds of formula (I) wherein X represents a bond may be prepared by a process which comprises reacting a compound of formula (XII):

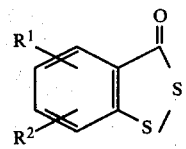
(XII)

wherein $R^1$ and $R^2$ are as defined with respect to formula (I) above; with an amine $R.NH_2$ wherein R is as defined with respect to formula (I) above.

This reaction may conveniently be carried out in a lower alcohol at elevated temperatures.

Compounds of formula (I) wherein R represents a nitrogen-containing heterocyclic ring attached to the group X via the ring nitrogen, or a group $-NH.R^3$ may be prepared by reacting a compound of formula (XIII):

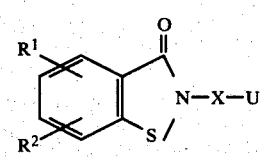
(XIII)

wherein $R_1$, $R^2$ and X are as defined with respect to formula (I) above and U represents a readily displaceable group; with a compound of formula (XIVA) or (XIVB):

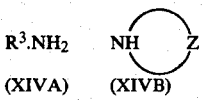

(XIVA)    (XIVB)

$R^3$ is as defined with reference to formula (I) above, and Z is the residue of a heterocyclic ring.

Suitably the group U is a halogen atom, for example chlorine or bromine; a substituted sulphonyloxy group, for example p-toluenesulphonyloxy or methanesulphonyloxy.

The reaction may suitably be carried out in a hydrocarbon solvent such as toluene at an elevated temperature for example 100°-120°.

The invention also provides a pharmaceutical composition which comprises a compound of formula (I) as defined above together with at least one pharmaceutically acceptable carrier.

As is common practice, such compositions will usually be accompanied by or associated with written or printed directions for use in the medical treatment concerned, in this case as an agent for the inhibition of platelet aggregation or thrombus formation.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol, or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; nonaqueous vehicles (which may include edible oils), for example almond oil, fractionated coconut oil, oily esters such as glycerine, porpylene glycol, or ethyl alcohol; preservatives, for example methyl or propyl p-hydroxybenzoate or sorbic acid, and if desired conventional flavouring or colouring agents. The compound may also if desired by incorporated in a foodstuff, for example in the form of a biscuit.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. Where the compositions comprise dosage units, each unit will preferably contain from 1–500 mg., of the active ingredient.

The dosage employed for adult treatment will of course depend on the dose-response characteristics of the particular active ingredient, and also on the blood volume and condition of the patient, but will normally be in the range 0.01 to 30 mg/kg/day depending on the route and frequency of administration. The preferred dose is 10 to 500 mg., orally 1 to 3 times a day for an adult human.

The compositions of the invention are useful for administration to humans and animals to prevent clot formation for example after surgery to prevent postoperative thrombosis; in geriatric patients to prevent transient cerebral ischemic attacks; and long-term prophylaxis following myocardial infarcts and strokes.

The compounds of formula (I) may also have applications in the storage of whole blood in blood banks, and whole blood to be used in heart-lung machines, or to be circulated through organs, e.g. heart and kidneys, which have been removed from a cadaver and prior to transplant.

Accordingly, this invention also provides a process for inhibiting platelet aggregation in vitro comprising the addition of a compound of the formula (XV) or a pharmacologically acceptable acid addition salt of such a compound having a basic nitrogen atom in the molecule:

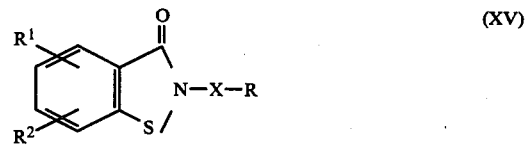

(XV)

wherein
$R^1$ and $R^2$ are the same or different and each is hydrogen, a lower alkyl, lower alkoxy, halo-lower alkyl, nitro, amino, acylamino or halogen, or $R^1$ together with $R^2$ when attached to adjacent carbon atoms represent a $C_3$–$C_6$ alkylene or oxy($C_1$–$C_3$)alkyleneoxy moiety;
X represents a bond or a straight or branched chain alkylene group having from one to twelve carbon atoms; and
R represents a nitrogen-containing heterocyclic ring, or a group of formula —NH.$R^3$ wherein $R^3$ is a nitrogen-containing heterocyclic ring the groups R and $R^3$ being optionally substituted with a lower alkyl, carboxy or alkoxycarbonyl group; to whole blood or platelet-rich concentrates.

The dosage for such an addition is preferably from 0.01 to 50 micrograms/ml of whole blood.

The invention also provides a composition comprising whole blood and a compound of formula (XV) above or a pharmacologically acceptable acid addition salt of such a compound having a basic nitrogen atom in the molecule.

The following Examples illustrate the preparation of some of the compounds of this invention.

EXAMPLE 1

5-Chloro-2[β-(2-pyridyl)ethyl]-1,2-benzisothiazol-3-one hydrochloride

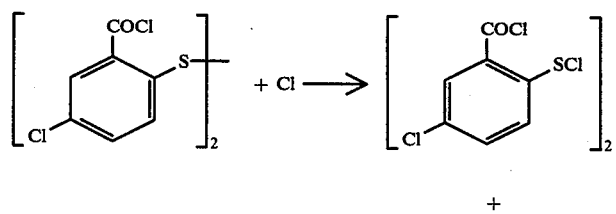

+

-continued

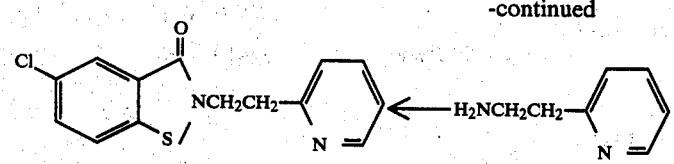

To a suspension of 5,5'-dichloro-2,2'-dithiodibenzoyl-chloride (4.12 g. 0.01 mole) in dry CCl$_4$ (100 ml), chlorine was passed until solution was complete (approx. 1½ hours) and excess chlorine removed by passing nitrogen through the solution. The solution was then filtered and added to a solution of 2-(2-aminoethyl)pyridine (7.32 g, 0.05 M) in dry CCl$_4$ (100 ml) in a three necked 500 ml. round bottomed flask fitted with a drying tube and stirred. After the addition was complete (about ¼ hour), the solution was stirred at room temperature for a further hour. The reaction mixture was washed with water and then extracted with 2 N HCl solution. The acid extract was basified with 2 N sodium hydroxide solution and extracted with dichloromethane. The organic extract was dried over Mg SO$_4$, filtered and the solvent evaporated to yield the crude free base. This was dissolved in isopropyl alcohol and hydrogen chloride was passed into the solution to form the salt. After removal of isopropanol under reduced pressure the resulting hydrochloride salt was recrystallised from ethanol. (3.5 g. 68%) Mpt. 178°–81° C.

EXAMPLE 2

2-[6-(3-azabicyclo[3.2.2]non-3-yl)-hexyl]-1,2-benziso-thiazlol-3-one hydrochloride

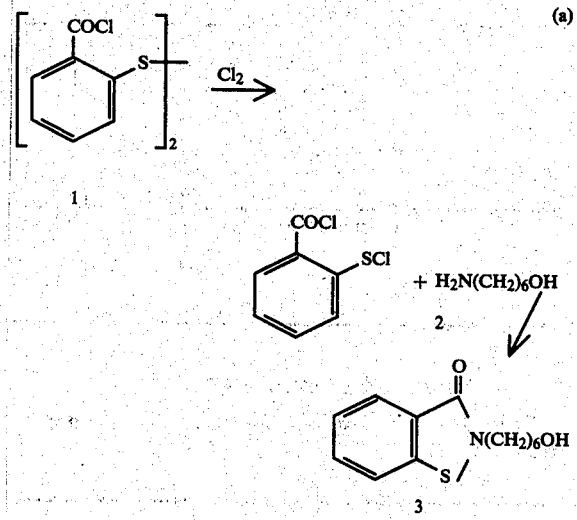

Chlorine was passed into a suspension of 2,2'-dithiodibenzoyl chloride (6.8 g. 0.01 mole) (1) in dry CCl$_4$ (100 ml) until solution was complete then excess chlorine removed in a stream of nitrogen. The solution was then filtered and added slowly with stirring to a solution of 6-amino-hexanol (7.02 g, 0.06 moles) in dry CCl$_4$ (100 ml) at 0° C. After the addition was complete (30 minutes), the mixture was stirred at room temperature for a further hour then washed with water. The organic solution was dried (anhyd. Mg SO$_4$) and filtration and removal of the solvent under reduced pressure yielded 3 as an un-crystallisable gum, pure by thin layer chromatography (4.8 g. 92%). The infra-red and proton magnetic resonance spectra was consistant with the proposed structure.

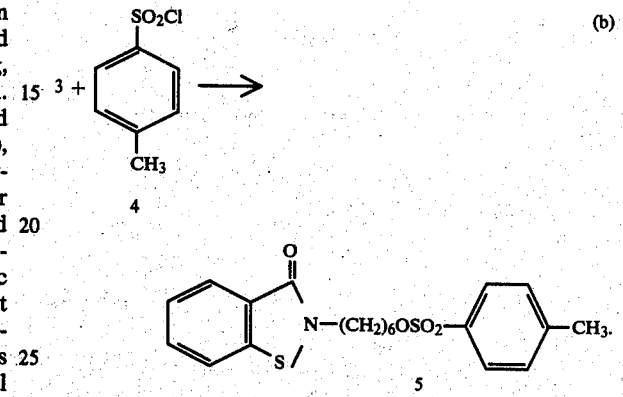

To a solution of 2-(6-hydroxyhexyl)-1,2-benziso-thiazol-3-one (5 g. 0.02 mole) (30 in pyridine (30 ml) at 0° C. p-toluenesulphonyl chloride (7.6 g) was added (4) maintaining the temperature of the reaction mixture at 0° with external cooling. The reaction mixture was allowed to stand at room temperature for 12 hours and was then poured into ice/water. The product 5 was isolated by extraction with dichloromethane in the usual manner. The crude product was taken up in ethanol treated with activated carbon and filtered through celite. Evaporation of the ethanol yielded pure 5 as an un-crystallizable gum pure by thin layer chromatography infra-red and proton magnetic spectra. Yield 7.2 g. 90%.

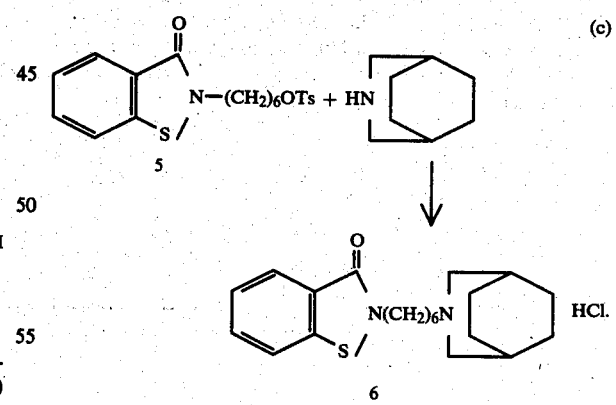

A solution of the tosylate 5 (4.05 g. 0.01 mole) and 3-azabicyclo[3.2.2]nonone (1.25 g. 0.01 mole) in toluene (100 ml) were heated under reflux for 5 hours then cooled. The mixture was then extracted with 10% HCl solution and the acid extract basified with 10% sodium hydroxide solution. The crude of 6 was isolated by extraction with dichloromethane in the usual manner. The hydrochloride salt was prepared by dissolving the crude base in isopropyl alcohol and passing hydrogen chloride gas into the solution. Removal of the solvent yielded a gum which solidified on trituration with acetone. Recrystallisation of the solid from ethanol yielded pure 6 (3.4 g. 72%) m.p. 167°–9°.

EXAMPLE 3

5,6-Dimethoxy-2[β-(2-pyridyl)ethyl]-1,2-benzisothiazol-3-one

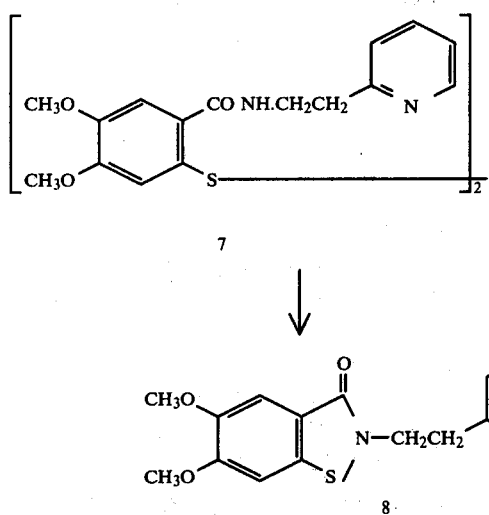

To a suspension of 4,4',5,5'-tetramethoxy-2,2'-dithiodibenzoylchloride (2.0 g, 4.32 mmole) in dry ether (100 ml) containing pyridine (4 ml) was added 2-(2-aminoethyl)pyridine (1.60 g. 13.0 mmole) in dry ether (50 ml) dropwise with stirring at room temperature. The mixture was stirred for 1 hour and allowed to stand for 18 hours before the solvent was evaporated under reduced pressure. A solution of the residue in dichloromethane was washed with water and then shaken with 2 N hydrochloric acid. The acid layer was basified with 10% aqueous sodium hydroxide solution and the mixture was extracted twice with dichloromethane. The organic extracts were combined and dried over magnesium sulphate. Removal of the solvent gave a yellow solid which was recrystallised from isopropanol yielding the product 6 as cream coloured needles (1.18 g, 43%) m.p. 154.5°–156.5°.

EXAMPLE 4

2-[2'-Pyridylaminomethyl]-1,2-benzisothiazol-3-one

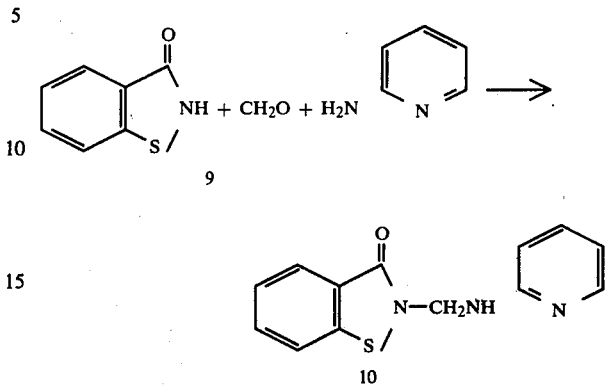

To a solution of 1,2-benzisothiazol-3-one (9) (1.5 g., 0.01 mole) and 2-aminopyridine (1 g., 0.0106 mole) in ethanol (20 ml) formalin solution (2 ml) was added and the mixture allowed to stand at room temperature for three days. After removal of the solvent under reduced pressure the residue was taken up in ether and washed with water. The ether layer was dried (Mf $SO_4$) and after removal of the ether the crude product was crystallised from EtOH to yield pure 10 (0.55 g., 27%) m.p. 168–170 dec.

EXAMPLES 5–8

The following compounds were prepared using the method as described in Example 1:

| Example No. | $R^1$ | $R^2$ | $R^5$ | m.p. (°C.) | yield (%) |
|---|---|---|---|---|---|
| 5. | H | H | morpholinyl | 122–3° | 60 |
| 6. | Cl | H | 2-pyridyl | 239°–239.5° | 55 |
| 7. | Cl | H | 2-pyrimidinyl | 275–9° | 31 |
| 8. | H | H | thiazol-2-yl | 240.2° | 32 |

EXAMPLES 9–21

The following compounds were prepared using the method shown:

| Example No. | $R^1$ | $R^2$ | R | m.p. (°C.) | Yield (%) | Prepared by method of Example No. |
|---|---|---|---|---|---|---|
| 9. | H | H | 2-pyridyl.HCl. | 183–5° | 62 | 1. |
| 10. | $CH_3$ | H | 2-pyridyl.HCl. | 176–8° | 65 | 1. |
| 11. | H | Cl | 2-pyridyl.HCl. | 172–3° | 58 | 1. |
| 12. | Cl | Cl | 2-pyridyl | 167.5–70° | 35 | 3. |
| 13. | H | H | 3-azabicyclo[3.2.2]-non-3-yl.HCl. | 238–245° (Dec) | 80 | 2. |
| 14. | Cl | Cl | 3-azabicyclo[3.2.2]-non-3-yl | 160–2° | 60.5 | 2. |

-continued

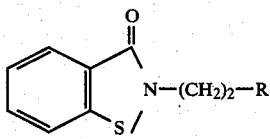

| Example No. | R¹ | R² | R | m.p. (°C.) | Yield (%) | Prepared by method of Example No. |
|---|---|---|---|---|---|---|
| 15. | CH₃O— | CH₃O— | 3-azabicyclo[3.2.2]-non-3-yl.HCl. | 229–32° | 63 | 3. |
| 16. | Cl | Cl | 1-pyrrolidinyl | 152.5–154.5° | 38 | 1. |
| 17. | Cl | Cl | 1-pyrrolidinyl HCl | 243–5° (Dec) | 17 | 1. |
| 18. | CH₃O— | CH₃O— | 1-pyrrolidinyl HCl | 223–5° | 39 | 3. |
| 19. | H | H | 1-homopiperidinyl HCl. | 178–80° | 55 | 2. |
| 20. | H | H | N—4 1,2,3,4-tetrahydro-isoquinolyl.HCl. | 180–95° (Dec) | 60 | 2. |
| 21. | H | H | 1,2-benzisothiazol-3-on-2-yl | 210–11° | 50 | |

EXAMPLES 22–23

The following compounds were prepared using the method as described in Example 4:

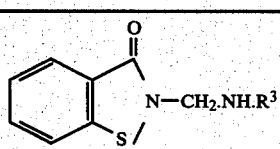

| Example No. | R₃ | m.p. (°C.) | yield (%) |
|---|---|---|---|
| 22. | (4-ethoxycarbonyl)thiazol-2-yl | 234–6° | 39 |
| 23. | 4-pyridyl | 218–9° | 28 |

EXAMPLES 24–25

The following compounds were prepared using the method as described in Example 1:

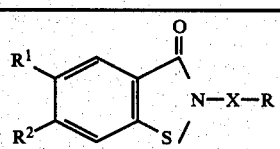

| Example No. | R¹ | R² | X | R | m.p. (°C.) | Yield (%) |
|---|---|---|---|---|---|---|
| 24. | Cl | Cl | —CH₂— | 3-pyridyl | 208° | 25 |
| 25. | CH₃ | H | —(CH₂)₂— | 1-pyrrolidinyl (oxalate salt) | 165° | 53 |

EXAMPLES 26–27

The following compounds were prepared using the method as described in Example 2:

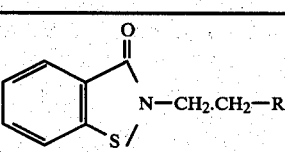

| Example No. | R | m.p. (°C.) | Yield (%) |
|---|---|---|---|
| 26 | tetrahydroquinolyl (hydrochloride)½H₂O. | 180–195 (dec) | 50 |
| 27 | 2-methylpiperidinyl | 223–5 | 43 |

-continued

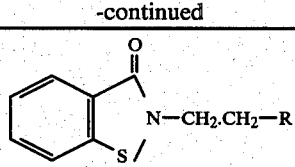

| Example No. | R | m.p. (°C.) | Yield (%) |
|---|---|---|---|
| (hydrochloride) | | | |

EXAMPLE 28

5,6-Dimethyl-1-(β-1-pyrrolidinylethyl)-1,2-benzisothiazol-3-one was prepared using the method as described in Example 3, melting point 105°–107° C.

EXAMPLE 29

Preparation of 2-β-(4-methyl-2-thiazolyl)ethyl-1,2-benzisothiazol-3-one

To a stirred suspension of N,N'-bis-[2-(4-methyl-2-thiazolyl)ethyl]-2,2'-dithio-bis-benzamide (3.1 g., 5.6 mmole) in carbon tetrachloride (50 ml) a solution of bromine (0.89 g., 5.6 mmole) in carbon tetrachloride (10 ml) was added in one portion. The mixture was stirred at room temperature for 10 minutes. The resulting o-bromothiol-N-[2-(4-methyl-2-thiazolyl)ethyl]-benzamide was filtered off, washed with carbon tetrachloride then suspended in glacial acetic acid (30 ml) and heated under reflux for 20 minutes. The reaction mixture was cooled, the acetic acid removed under vacuume and the residue basified with 10% aqueous sodium hydroxide solution. The mixture was diluted with water (50 ml), extracted with dichloromethane (2×50 ml) and the organic phase dried (anhyd. MgSO₄). Removal of the drying agent and solvent yielded a gum (3 g) which after chromatography on alumina with dichloromethane as eluant, yielded pure 2-β-(4-methyl-2-thiazolyl)ethyl-1,2-benzisothiazol-3-one, 2.1 g., m.p. 82°–83°, yield 68%.

EXAMPLE 30

2-β-(4-Methyl-2-thiazolyl)ethyl-5-methyl-1,2-benzisothiazol-3-one was prepared in a similar manner to that described in Example 29. m.p. 129–130. Yield 42%.

EXAMPLE 31

Preparation of
5-methyl-2-(β-2'-pyridylethyl)-1,2-benzisothiazol-3-one

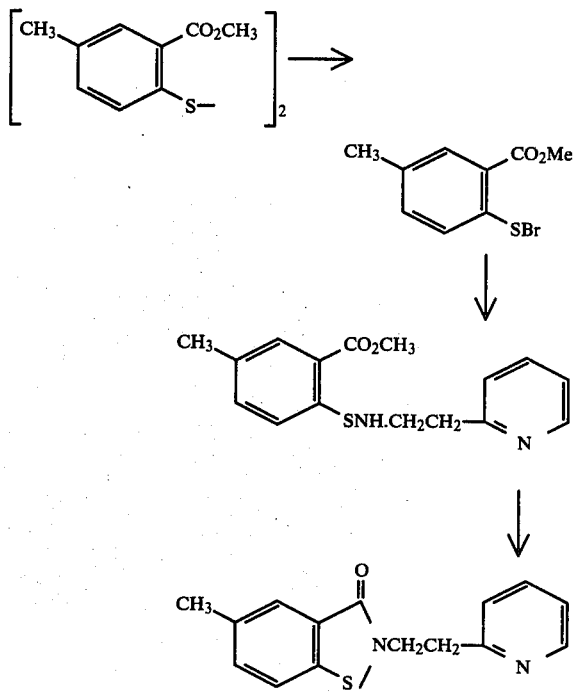

To a stirred suspension of dimethyl 2,2'-dithio-5,5'-dimethyldibenzoate (5 g., 4 mmole) in carbon tetrachloride (35 ml) at room temperature, a solution of bromine (2.21 g., 14 mmole) in the same solvent (20 ml) was added over 15 minutes. The mixture was stirred at room temperature for a further 30 minutes, then added dropwise to a solution of 2-(2-aminoethyl) pyridine (3.52 g., 29 mmole) and triethylamine (2.93 g., 29 mmole) in carbon tetrachloride (35 ml) over 15 minutes. Stirring was continued for a further 30 minutes, then the mixture was heated under reflux for 1 hour. The reaction mixture was cooled, diluted with chloroform (100 ml), and washed well with water (2×100 ml). The organic layer was dried (anhyd. MgSO4). Removal of the solvent yield N-(β-2'-pyridylethyl)-2-methoxycarbonyl-4-methylbenzenesulphenamide as an oil (9.45 g).

This crude material in ethanol (40 ml) was treated with a solution of sodium hydroxide (0.12 g) in ethanol (10 ml) and the mixture heated under reflux for 2 hours. The ethanol was removed under reduced pressure and the residue partitioned between water (100 ml) and chloroform (50 ml). The organic layer was washed with water (100 ml), dried, (anhyd. MgSO4) and the solvent removed under reduced pressure. The residue was purified by chromatography on alumina using dichloromethane as eluant yielding 5-methyl-2-(β-2'-pyridylethyl)-1,2-benzisothiazol-3-one (5.0 g., 67%), m.p. 103°–105° C. (aq. EtOH).

BIOLOGICAL DATA

The compounds of the Examples above were tested for their ability to inhibit platelet aggregation in vitro as follows:

Human blood (20 ml) is drawn into a plastic syringe and immediately anti-coagulated by mixing with 0.1 volumes of 3.8% (w/v) trisodium citrate dihydrate. Platelet-rich-plasma (PRP) is prepared by centrifuging the anti-coagulated blood at 180 g., for 12 minutes, at room temperature. Collagen (3×-bovine achilles tendon) is suspended in 0.9% (w/v) saline, using a commercially available mixer emulsifier. PRP was mixed with 0.1 volumes saline (control) or compound dissolved in saline and incubated at 37° for 3 minutes, before the addition of collagen. Water-insoluble compounds were added to PRP, dissolved in 0.005 volumes dimethylformamide, the solvent being included in controls when appropriate. The final concentration of each compound was 100 μM.

Platelet aggregation in response to collagen was measured photometrically (Born, G. V. R., 1962, Nature, 194, 927) in a Bryston aggregometer coupled to a Vitatron linear pen recorder. The activity of each compound was expressed as percentage inhibition of the aggregation response to a dose of collagen producing a just-maximal change in light transmission in control PRP.

The results are shown in Table I.

TABLE 1

| Compound of Example No. | % Inhibition | Compound of Example No. | % Inhibition |
|---|---|---|---|
| 1 | 100 | 14 | 100 |
| 2 | 100 | 15 | 92 |
| 3 | 100 | 16 | 100 |
| 4 | 100 | 17 | 100 |
| 5 | 100 | 18 | 91 |
| 6 | 100 | 19 | 92 |
| 7 | 100 | 20 | 100 |
| 8 | 100 | 21 | 91 |
| 9 | 100 | 22 | 100 |
| 10 | 100 | 23 | 23 |
| 11 | 100 | 26 | 100 |
| 12 | 100 | 27 | 100 |
| 13 | 100 | 31 | 100 |

I claim:

1. A method of inhibiting platelet aggregation in humans and animals, of inhibiting thromboses in humans and animals and for treating arterial thromboses in humans and animals which comprises administering to a human or animal in need thereof, in an amount sufficient to inhibit platelet aggregation, an amount sufficient to inhibit the formation of thrombs or an amount sufficient to dissolve thromboses, a compound of the formula

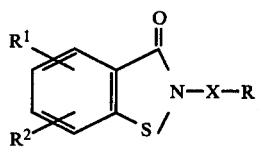

or a pharmaceutically acceptable non-toxic acid addition salt thereof when there is a basic nitrogen atom in the molecule, wherein $R^1$ and $R^2$ are the same or different and each is hydrogen, lower alkyl, lower alkoxy, halo-lower alkyl, nitro, amino, acetylamino or halogen; or $R^1$ together with $R^2$ when attached to adjacent carbon atoms form an alkylene moiety of 3 to 6 carbon atoms or an oxyalkyleneoxy moiety of 1 to 3 carbon atoms; X is a bond or a straight or branched chain alkylene of 1 to 12 carbon atoms; and R is pyrrolidinyl, unsubstituted or substituted by one lower alkyl, carboxy or alkoxycarbonyl of 1 to 6 carbon atoms in the alkoxyl moiety, or a group of the formula—$NH.R^3$ wherein $R^3$ is pyrrolidinyl, unsubstituted by one lower alkyl, carboxy or alkoxycarbonyl of 1 to 6 carbon atoms in the alkoxyl moiety, provided that R¹ and R² are not hydrogen or lower alkyl when X is alkylene of two carbon atoms and R is unsubstituted pyrrolidinyl.

2. A method according to claim 1 wherein R¹ and R² are the same or different and each is lower alkoxy, halo-lower alkyl or halogen.

3. A method according to claim 1, wherein R¹ and R² are the same or different and each is lower alkoxy or halogen.

4. A method according to claim 3, wherein R¹ and R² are in the 5- and 6- positions.

5. A method according to claim 1, wherein the compound is in the form of an acid addition salt selected from the group consisting of a sulphate, nitrate, phosphate, borate, hydrochloride, hydrobromide, hydroiodide, acetate, oxalate, tartrate, maleate, citrate, succinate, benzoate, ascorbate, methane sulphonate and p-toluene sulphonate.

6. A method according to claim 1, wherein X is methylene, ethylene, propylene, n-butylene, n-pentylene, n-hexylene, n-dodecylene, 1-methylethylene, 1- or 2-methylpropylene, isopropylene or isobutylene.

7. A method according to claim 1, wherein X is straight or branch chain alkylene of 1 to 6 carbon atoms.

8. A method according to claim 1, wherein X is alkylene of 2 carbon atoms.

9. A method according to claim 1, wherein R¹ and R² are the same or different and each is methoxy, ethoxy, n-propoxy, iso-propoxy, n-butoxy, sec-butoxy, iso-butoxy, tert-butoxy, chloro, bromo, fluoro, or trifluoromethyl.

10. A method according to claim 1, wherein R¹ is chloro.

11. A method according to claim 1, wherein R¹ and R² are the same or different and each is methoxy, or chloro.

12. A method according to claim 1, wherein the compound is of the formula

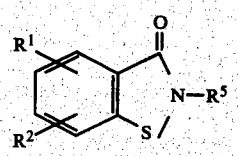

or a pharmaceutically acceptable non-toxic acid addition salt thereof when there is a basic nitrogen atom in the molecule wherein R¹ and R² are the same or different and each is hydrogen, lower alkyl, lower alkoxy, halo-lower alkyl, nitro, amino, acetylamino or halogen; or R¹ together with R² when attached to adjacent carbon atoms form an alkylene moiety of 3 to 6 carbon atoms or an oxyalkyleneoxy moiety of 1 to 3 carbon atoms; and R⁵ is pyrrolidinyl, unsubstituted or substituted by one lower alkyl, carboxy or alkoxycarbonyl of 1 to 6 carbon atoms in the alkoxyl moiety provided that R¹ and R² are not hydrogen or lower alkyl when x is alkylene of two carbon atoms and R is unsubstituted pyrrolidinyl.

13. A method according to claim 1, wherein the compound is of the formula

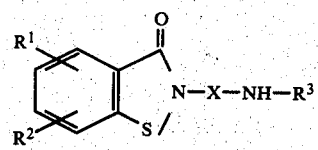

or a pharmaceutically acceptable non-toxic acid addition salt thereof when there is a basic nitrogen atom in the molecule, wherein R¹ and R² are the same or different and each is hydrogen, lower alkyl, lower alkoxy, halo-lower alkyl, nitro, amino, acetylamino or halogen; or R¹ together with R² when attached to adjacent carbon atoms form an alkylene moiety of 3 to 6 carbon atoms or an oxylkyleneoxy moiety of 1 to 3 carbon atoms; X is a bond or a straight or branched chain alkylene of 1 to 12 carbon atoms; and R³ is pyrrolidinyl, unsubstituted or substituted by one lower alkyl, carboxy or alkoxycarbonyl of 1 to 6 carbon atoms in the alkoxyl moiety.

14. The method according to claim 1, wherein R and R³ is 1-pyrrolidino.

15. The method according to claim 14, wherein said compound is 5,6-dichloro-2-[β-(1-pyrrolidinyl)ethyl]-1,2-benzisothiazol-3-one.

16. The method according to claim 14, wherein said compound is 5,6-dichloro-2-[β-(1-pyrrolidinyl)ethyl]-1,2-benzisothiazol-3-one hydrochloride.

17. The method according to claim 14, wherein said compound is 5,6-dimethoxy-2-[β-(1-pyrrolidinyl)ethyl]-1,2-benzisothiazol-3-one.

18. The method for inhibiting platelet aggregation in vitro which comprises adding a compound of the formula

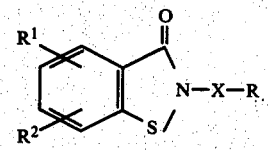

or a pharmaceutically acceptable acid addition salt thereof when there is a basic nitrogen atom in the molecule wherein R¹ and R² are the same or different and each is hydrogen, lower alkyl, lower alkoxy, halo-lower alkyl, nitrogen, amino, acetylamino or halogen; or R¹ and R² when attached to adjacent carbon atoms form an alkylene moiety of 3 to 6 carbon atoms or an oxy-alkyleneoxy moiety of 1 to 3 carbon atoms, X is a bond or straight or branched chain alkylene of 1 to 12 carbon atoms; and R is pyrrolidinyl, unsubstituted or substituted by one lower alkyl, carboxy or alkoxycarbonyl of 1 to 6 carbon atoms in the alkoxy moiety, or a group of the formula —NH.R³, wherein R³ is pyrrolidinyl, unsubstituted or substituted by one lower alkyl, carboxy or alkoxycarbonyl of 1 to 6 carbon atoms in the alkoxyl moiety, to whole blood or platelet-rich concentrates.

19. A pharmaceutical composition useful for the inhibition of platelet aggregation and thrombus formation and for the treatment of arterial thromboses in humans and animals which comprises a platelet aggregation inhibitory amount, an amount sufficient to inhibit the formation of thrombs or an anti-arterial thrombotically effective amount of a compound of the formula

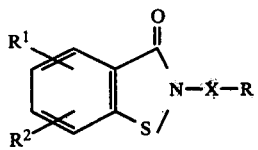

or a pharmaceutically acceptable non-toxic acid addition salt thereof when there is a basic nitrogen atom in the molecule, wherein $R^1$ and $R^2$ are the same or different and each is hydrogen, lower alkyl, lower alkoxy, halo-lower alkyl, nitro, amino, acetylamino or halogen; or $R^1$ together with $R^2$ when attached to adjacent carbon atoms form an alkylene moiety of 3 to 6 carbon atoms or an oxyalkyleneoxy moiety of 1 to 3 carbon atoms; X is a bond or a straight or branched chain alkylene of 1 to 12 carbon atoms; and pyrrolidinyl, unsubstituted or substituted by one lower alkyl, carboxy or alkoxycarbonyl of 1 to 6 carbon atoms in the alkoxyl moiety, or a group of the formula —NH.$R^3$ wherein $R^3$ is pyrrolidinyl, unsubstituted or substituted by one lower alkyl, carboxy or alkoxycarbonyl of 1 to 6 carbon atoms in the alkoxyl moiety, provided that when $R^1$ and $R^2$ are at positions 5 and 7 and are hydrogen or halogen and X is lower alkylene, then R is not pyrrolidinyl which is attached via a nitrogen atom thereof to X; in combination with a pharmaceutically acceptable carrier provided that $R^1$ and $R^2$ are not hydrogen or lower alkyl when x is alkylene of two carbon atoms and R is unsubstituted pyrrolidinyl.

* * * * *